United States Patent [19]
Abelson et al.

[11] Patent Number: 5,431,907
[45] Date of Patent: Jul. 11, 1995

[54] TREATMENT OF VASCULAR DISORDERS OF THE POSTERIOR SEGMENT OF THE EYE BY TOPICAL ADMINISTRATION OF CALCIUM CHANNEL BLOCKING AGENTS

[76] Inventors: Mark B. Abelson, 26 Phillips St., Andover, Mass. 01810; Richard L. Giovanoni, 220 Richmond St., E. Taunton, Mass. 02718

[21] Appl. No.: 285,300

[22] Filed: Aug. 3, 1994

[51] Int. Cl.⁶ .............................................. A61K 31/35
[52] U.S. Cl. ................................ 424/78.04; 424/427; 514/912; 514/913; 514/914; 514/915; 514/929
[58] Field of Search ...................... 424/400, 78.04, 427; 514/912–915, 929

[56] References Cited

U.S. PATENT DOCUMENTS

| | | | |
|---|---|---|---|
| 4,525,346 | 6/1985 | Stark | 424/80 |
| 4,966,773 | 10/1990 | Gressel et al. | 424/489 |
| 4,981,871 | 1/1991 | Abelson | 514/523 |
| 5,221,690 | 6/1993 | Sugiyama et al. | 514/573 |

*Primary Examiner*—Thurman K. Page
*Assistant Examiner*—Sharon Howard
*Attorney, Agent, or Firm*—Vorys, Sater, Seymour & Pease

[57] ABSTRACT

Ischemic disorders of the retina and associated tissues of the posterior segment of the eye are treated by topical administration to the eye of an amount of a calcium channel blocking agent effective to increase blood flow to those tissues. Calcium channel blocking agents of Class I are especially useful, and among these a preferred agent is verapamil hydrochloride.

12 Claims, No Drawings

TREATMENT OF VASCULAR DISORDERS OF THE POSTERIOR SEGMENT OF THE EYE BY TOPICAL ADMINISTRATION OF CALCIUM CHANNEL BLOCKING AGENTS

BACKGROUND OF THE INVENTION

1. Field of the Invention

This invention relates to treatment of diseases and/or disorders of the posterior segment of the eye and more particularly to the treatment of disorders arising from a decrease or failure of blood perfusion to the posterior ocular structures.

2. Description of the Prior Art

The mammalian eye is a generally spherical structure that performs its visual function by forming an image of an exterior illuminated object on a photosensitive tissue, the retina. The basic supporting structure for the functional elements of the eye is the generally spherical tough, white outer shell, the sclera, which is comprised principally of collagenous connective tissue and is kept in its spherical shape by the internal pressure of the eye. The anterior portion of the sclera supports and contains the elements that perform the function of focusing the incoming light, i.e., the cornea and crystalline lens, and the function of regulating the intensity of the light entering the eye, i.e., the iris. The posterior portion of the globe supports the retina and associated tissues. In the posterior portion of the globe immediately adjacent the interior surface of the sclera lies the choroid, a thin layer of pigmented tissue liberally supplied with blood vessels. The portion of the choroid adjacent its interior surface is comprised of a network of capillaries, the choriocapillaris, which is of importance in the supply of oxygen and nutrients to the adjacent layers of the retina. Immediately within the choroid lies the retina, which is the innermost layer of the posterior segment of the eye and receives the image formed by the refractive elements in the anterior portion of the globe. The photoreceptive rod and cone cells of the retina are stimulated by light falling on them and pass their sensations via the retinal ganglia to the brain.

Retinal function and health is dependent on two independent blood supplies. The outer portion of the retina, adjacent to the choroid, is nurtured primarily by the choriocapillaris of the choroid, while inner retinal layers receive their blood supply mainly via branches of the central retinal artery. Accordingly, both blood supplies are must be intact for proper perfusion of the retina, and one of them cannot substitute for the other.

Occlusive diseases or disorders of blood vessels servicing the retina affect the inner layers of the sensory retina most significantly and therefore concern blood vessels, i.e., arterioles and capillaries, that receive their blood supply from the central retinal artery. Normal perfusion of retinal tissues requires that vascular pressure in the retinal arteries, capillaries, and veins exceed the intraocular pressure of the eye in order to prevent the retinal vascular system from collapsing. Diseases or disorders that restrict or stop retinal blood perfusion can be localized and unique to the retina or reflective of systemic vascular diseases such as atherosclerosis. Regardless of etiology, compromised blood perfusion of retinal arteries to the extent that vascular pressure within the retina structure is less than IOP causes these arteries to collapse leading to retinal ischemia with accompanying coagulative necrosis of inner retinal layers and loss of visual function in the ischemic portions of the retina.

The prognosis of such a disorder is related to the cause(s), degree of obstruction and length of time the occlusion persists. Occlusions resulting from the effects of systemic vascular problems, such as atherosclerotic cardiovascular disease and hypertension, can cause entrapment of cholesterol emboli in the retinal artery causing lasting visual field defects. In contrast, episodes of occlusion by platelet emboli are typically brief, leaving no visual abnormality. In any case, treatment directed toward alleviating the nonperfusion condition having an acute onset needs to be effective within 3-4 hours following the episode; otherwise, irreversible visual defects will result.

Historically, patients with retinal artery obstruction have been treated by administration of 100% oxygen or carbogen (95% oxygen, 5% carbon dioxide) in an attempt to improve retinal oxygenation. However, because of irreversible adverse side effects associated with administering pure or high concentration oxygen, the duration of this therapy must be limited. Additionally, while gas therapy is designed to oxygenate retinal tissue, it does not promote blood perfusion per se. Clearly, because of (i) the need to initiate this sophisticated response treatment quickly, and (ii) its potential side effects, there is need for a more readily available, practical and safer treatment regimen that focuses on prevention of the episode rather than responding to the episode.

In general, retinal disorders characterized by retinal ischemia and therefore responsive to improved blood flow include, but are not limited to:
(i) diabetic retinopathy
(ii) central retinal artery occlusion
(iii) central retinal vein occlusion and resultant degenerative diseases of the retinal venous endothelium
(iv) senile macular degeneration
(v) ischemic optic neuropathies
(vi) transient central retinal occlusion Hitherto, certain treatments have been used with some success in delaying the progression of ophthalmic deterioration or even partially reversing the course of these diseases. Systemic drugs that increase the blood flow to the retina have been found to have some effect in alleviating the progression of such conditions as diabetic retinopathy. In particular, systemic, e.g., oral, administration of calcium channel blocking agents has been found to be of some benefit in treating conditions due to poor blood flow in the posterior segment of the eye. However, the systemic administration of vasoactive drugs in order to treat a condition specific to certain structures of the eye is subject to the evident disadvantage that undesirable systemic side effects may be induced. Hitherto it has not been known that topical administration of calcium channel blocking agents can improve blood flow to the posterior segment of the eyeball and thereby arrest or alleviate the deterioration of vision associated with retinal conditions caused by deficient retinal blood flow.

Although it is well known to apply topical medications to treat ophthalmic disorders caused by dysfunction of tissues in the anterior region of the eye, topical application of medication has not been generally found effective to treat ophthalmic pathologic conditions of tissues and structures located in the posterior region of the eye.

Accordingly, a need has continued to exist for a method of treating diseases and disorders of the posterior segment of the eye caused by poor blood flow by topical administration of an effective ophthalmic medicament.

SUMMARY OF THE INVENTION

This need has now been met by the method of the invention according to which disorders of the posterior segment of the eye due to deficient blood flow are treated by topical administration to the eye of an amount of a calcium channel blocking agent effective to increase blood flow to the posterior segment of the eye.

Accordingly, it is an object of the invention to provide a method for treatment of ischemic disorders of the posterior segment of the eye.

A further object is to provide a method for treatment of ischemic disorders of the posterior segment of the eye by topical administration of a drug that increases blood flow to the posterior segment of the eye.

A further object is to provide a method for treatment of ischemic disorders of the posterior segment of the eye by topical administration of a calcium channel blocking agent.

Other objects will become apparent from the description of the invention which follows.

DETAILED DESCRIPTION OF THE INVENTION AND PREFERRED EMBODIMENTS

According to the invention, the pathological ophthalmic conditions associated with decreased blood flow to the posterior segment of the eye are alleviated, or the progressive deterioration in ophthalmic function delayed, by topical administration of an amount of a calcium channel blocking agent effective to increase blood flow to the posterior segment of the eye. The increase in blood flow produced by topical application of calcium channel blocking agents can stop or reverse the loss in visual function associated with ischemic conditions of the retina and/or associated structures in the posterior segment of the eye.

Topical administration of a calcium channel blocking agent according to the invention is useful as a therapeutic measure for prophylaxis against retinal and/or choroidal vascular conditions predisposing toward disease, as well as retinal diseases and disorders responsive to maintenance of normal physiologic blood perfusion or at least improvement of blood perfusion from the levels associated with the disease condition in the retina and associated support structures.

The effective dose of calcium channel blocking agent used in the method of this invention will vary depending on the particular patient, the particular calcium channel blocking agent used and the mode of administration. The topical dose applied by instillation into the eye will typically range from about 10 micrograms to about 1 milligram per eye per day. The topical dose will generally be applied by instillation of the drug in a suitable vehicle 2–4 times per day.

The calcium channel blocking agent is administered topically in solution in any conventional aqueous pharmaceutically acceptable ophthalmic vehicle. The vehicle may be any vehicle that is not incompatible with the drug, e.g., conventional physiological saline solution containing 0.9% sodium chloride by weight. A physiological saline buffered with a suitable buffering agent, e.g., a phosphate buffer, to maintain approximately physiological pH is a suitable vehicle. Typically the concentration of the calcium channel blocking agent in the vehicle will vary from about 0.1 mg/ml to about 10 mg/ml. Preferably the concentration of the drug in the solution is adjusted to deliver the desired dose of active ingredient in a single drop e.g., of about 40 microliters.

The calcium channel blocking agent may be delivered to the eye on any dosage schedule that is found to be effective. Typically the dosage schedule is determined by the duration of effectiveness of the particular active agent. For example, the dosage regimen may comprise one drop of an aqueous solution of the calcium channel blocking agent instilled into the affected eye from one to four times per day.

Topical administration of the calcium channel blocking agent may also be carried out by means of a controlled release dosage form inserted into the eye. Such devices are well known in the art and may comprise, e.g., a dispersion or solution of the drug in a polymeric matrix which is formed into a suitable lamella and inserted into the cul-de-sac of the conjunctiva where it slowly releases the medication over a period of time until the matrix is dissolved or removed after the drug is exhausted.

Calcium channel blocking agents are currently classified into six classes, based on the physiological effect produced by systemic administration. Class I calcium channel blocking agents include verapamil, gallopamil, anipamil and the like. Class II agents include nifedipine, nicardipine, nimodipine, nitrendipine and the like. Class III agents include diltiazem and compounds with similar activity. Class IV agents include flunarizine, cinnarizine and the like. Class V agents include prenylamine, fendiline and the like. Class VI agents include perhexiline and compounds having similar activity.

Preferred calcium channel blocking agents are those of Class I. Within Class I a preferred calcium channel blocking agent is verapamil hydrochloride. Verapamil hydrochloride may be administered in an aqueous solution containing from about 0.1% to about 1.0% by weight of the active ingredient. Preferably verapamil hydrochloride is administered in an aqueous solution containing 0.25% of verapamil hydrochloride by weight.

A preferred ophthalmic solution containing verapamil hydrochloride for use in practicing the method of this invention comprises verapamil hydrochloride dissolved in an aqueous solution containing the following buffers in the specified concentration ranges, wherein all percentages are by weight:

| | |
|---|---|
| boric acid | 0.5–3.0% |
| disodium edetate | 0.08–0.5% |
| dextrose | 0.1–5.0% |
| poly(vinylpyrrolidone) (PVP) | 1.0–4.0% |
| water, q.s. ad | 100% |

A particularly preferred formulation of the invention comprises verapamil HCl in an aqueous solution of the following ingredients, wherein all percentages are by weight:

| | |
|---|---|
| boric acid | 2.8% |
| disodium edetate | 0.18% |
| dextrose | 0.3% |
| poly(vinylpyrrolidone) (PVP) | 2.0% |

| | |
|---|---|
| water, q.s. ad | 100% |

Additionally, benzalkonium chloride (BAC) can be included in the ophthalmic solution as an antimicrobial agent to maintain the sterility of the packaged solution in multidose containers. If the solution is packaged in unit-of-use (one time use containers), the BAC may be omitted from the formulation.

EXAMPLE

This example illustrates the improvement of optic nerve blood flow in humans by topical administration of verapamil hydrochloride.

Blood flow in the optic nerve head of human volunteers having normal IOP was measured by the laser doppler technique. A group of 10 individual, after informed consent, was tested in a randomized double blind study by the following procedure.

For each experimental subject, before administration of the drug or control solution, the IOP was measured and the blood flow in the central retinal artery was examined by the laser doppler flow measurement technique and the mean Pourcelot's ratio, a measure of vascular resistance of the central retinal artery was determined. Subsequently, one drop of a 0.25% by weight solution of verapamil hydrochloride in an aqueous ophthalmic vehicle was instilled into an eye of each subject. Two hours after administration, the IOP and blood flow in the central retinal artery were again measured.

It was found that for the treated experimental subjects the mean Pourcelot's ratio was 0.77±0.02 which represents a reduction of 0.10±0.03 for the treated eyes as compared with a reduction of 0.02±0.03 for the untreated eyes. These results establish that topical administration of verapamil hydrochloride produces a significant reduction in the vascular resistance of the central retinal artery, and, consequently, increased blood flow to the optic nerve head. A mean reduction in IOP for the treated eyes of 11% was also observed.

This experiment establishes that the topical administration of a calcium channel blocking agent can effectively increase blood flow in the central retinal artery and thereby increase the perfusion of the retina to alleviate the damage thereto caused by poor blood flow.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method for treating ischemic disorders of the posterior segment of the eye comprising topically administering to the eye an amount of a Class 1 calcium channel blocking agent which is effective to increase blood flow in the central retinal artery.

2. The method of claim 1 wherein said Class I calcium channel blocking agent is verapamil hydrochloride.

3. The method of claim 1 wherein said Class I calcium channel blocking agent is administered in an aqueous ophthalmic solution comprising

| | |
|---|---|
| boric acid | 0.5–3.0% by weight |
| disodium edetate | 0.08–0.5% by weight |
| dextrose | 0.1–5.0% by weight |
| poly(vinylpyrrolidone) | 1.0–4.0% by weight. |

4. The method of claim 3 wherein said boric acid is present in a concentration of about 2.8% by weight.

5. The method of claim 3 wherein said disodium edetate is present in a concentration of about 0.18% by weight.

6. The method of claim 3 wherein said dextrose is present in a concentration of about 0.3% by weight.

7. The method of claim 3 wherein said poly(vinylpyrrolidone) is present in a concentration of about 2.0% by weight.

8. The method of claim 3 wherein said aqueous ophthalmic solution additionally comprises an amount of an ophthalmologically acceptable antimicrobial compound sufficient to preserve said aqueous ophthalmic solution from bacterial contamination.

9. The of claim 8 wherein said ophthalmologically acceptable antimicrobial compound is benzalkonium chloride.

10. The method of claim 3 wherein said aqueous ophthalmic solution comprises

| | |
|---|---|
| boric acid | 2.0% by weight |
| disodium edetate | 0.18% by weight |
| dextrose | 0.3% by weight |
| poly(vinylpyrrolidone) | 2.0% by weight. |

11. The method of claim 10 wherein said antimicrobial aqueous opthalmic solution additionally comprises an amount of an ophthalmologically acceptable antimicrobial compound an ophthalmologically acceptable antimicrobial compound sufficient to preserve said aqueous ophthalmic solution from bacterial contamination.

12. The method of claim 11 wherein said ophthalmologically acceptable antimicrobial compound is benzalkonium chloride.

* * * * *